United States Patent [19]
Hood

[11] Patent Number: 5,980,546
[45] Date of Patent: Nov. 9, 1999

[54] GUILLOTINE CUTTER USED WITH MEDICAL PROCEDURES

[75] Inventor: Larry L. Hood, Laguna Hills, Calif.

[73] Assignee: Nexus Medical System, Inc. LLC, Irvine, Calif.

[21] Appl. No.: 09/059,166

[22] Filed: Apr. 13, 1998

[51] Int. Cl.$^6$ .................................................... A61B 17/32
[52] U.S. Cl. ...................... 606/171; 606/175; 606/169; 604/22; 604/35
[58] Field of Search .................................. 606/171, 175, 606/169; 604/22, 35, 141

[56] References Cited

U.S. PATENT DOCUMENTS

| | | | |
|---|---|---|---|
| 5,106,364 | 4/1992 | Hayafuji et al. | 604/22 |
| 5,527,332 | 6/1996 | Clement | 606/171 |

*Primary Examiner*—Michael Buiz
*Assistant Examiner*—Lien Ngo
*Attorney, Agent, or Firm*—Blakely Sokoloff Taylor & Zafman

[57] ABSTRACT

A guillotine surgical cutter. The cutter includes an inner sleeve that moves within the inner channel of an outer sleeve. The distal end of the outer sleeve may have a plurality of outer ports. The inner sleeve may also have an inner channel and one or more openings that are in fluid communication with the outer ports of the outer sleeve. The inner sleeve can be connected to a diaphragm and a disk spring. The diaphragm may be adjacent to a drive chamber that is coupled to a source of pressurized air by a control valve. Actuation of the control valve pressurizes the drive chamber and moves the inner sleeve relative to the outer sleeve. The cutter may include a snap spring that is attached to the disk spring and which provides an additional acceleration of the inner sleeve. The springs return the inner sleeve back to the original position when the control valve is switched to reduce the pressure of the drive chamber.

6 Claims, 2 Drawing Sheets

GUILLOTINE CUTTER USED WITH MEDICAL PROCEDURES

BACKGROUND OF THE INVENTION

1. Field of the Invention

The present invention relates to a surgical cutter.

2. Background Information

There are many surgical procedures that require the cutting and aspiration of tissue. For example, in a retina re-attachment procedure the surrounding vitreo tissue must be removed before the retina is repaired. The cutting device must be delicate enough to remove the tissue without further damaging the retina. Vitrectomies are frequently performed with guillotine surgical cutters.

FIG. 1 shows a guillotine surgical cutter which include an inner sleeve 1 that moves relative to an outer port 2 of an outer sleeve 3. The sleeves 1 and 3 are coupled to a handpiece 4 that is held by a surgeon. The inner sleeve 1 is coupled to a vacuum system which pulls tissue into the outer port 2 when the inner sleeve 1 moves away from the port 2. The inner sleeve 1 then moves in a reverse direction past the outer port 2 to sever the tissue in a guillotine fashion. The vacuum system draws the severed tissue away from the outer port 2 so that the process can be repeated.

The inner sleeve 3 is connected to a diaphragm 5 and a return spring 6 that are rigidly attached to the handpiece 4. The diaphragm 5 is adjacent to a pneumatic drive chamber 7 that is in fluid communication with a source of pressurized air (not shown) that is controlled by a solenoid air valve (not shown).

In operation, the inner sleeve 1 is in an open position so that tissue is pulled into the outer port 2. The solenoid air valve is then opened to pressurize the drive chamber 7 and expand the diaphragm 5. Expansion of the diaphragm 5 moves the inner sleeve 1 so that the tissue within the outer port 2 is severed by the sleeve 1. Expansion of the diaphragm 5 also deflects the spring 6. The air valve is eventually switched to vent the drive chamber 7. The spring 6 then pulls the inner sleeve 1 back to the original position so that the process can be repeated.

The drive chamber 7 has a relative large amount of fluidic capacitance which limits the speed of the device. Additionally, the spring 6 becomes stiffer as the diaphragm 5 expands and moves the inner sleeve 1. The relative high fluidic capacitance and spring stiffness increases the pressure requirements for the drive chamber 7. Having to pressurize the drive chamber 7 to a higher level reduces the speed of the cutter. Many prior art guillotine cutters have a cut rate in the range of 500 cuts per minute (CPM). At these speeds the guillotine cutter tends to pull the tissue. It would be desirable to provide a guillotine cutter that operates at higher speeds than cutters of the prior art.

There is only one aspiration port in the outer sleeve and a single opening in the inner sleeve which perform the guillotine cutting action. The inner sleeve typically moves within the outer sleeve to fully close the outer port. Closing the outer port creates an instantaneous change in pressure which causes the remaining tissue to bounce back and send shock waves throughout the vitreous body. It would be desirable to provide a guillotine cutter that would minimize the bounce back effect of severing tissue within the port of the cutter.

SUMMARY OF THE INVENTION

The present invention is a guillotine surgical cutter. The cutter includes an inner sleeve that moves within the inner channel of an outer sleeve. The distal end of the outer sleeve may have a plurality of outer ports. The inner sleeve may also have an inner channel and one or more openings that are in fluid communication with the outer ports of the outer sleeve. The inner sleeve can be connected to a diaphragm and a disk spring. The diaphragm may be adjacent to a drive chamber that is coupled to a source of pressurized air by a control valve. Actuation of the control valve pressurizes the drive chamber and moves the inner sleeve relative to the outer sleeve. The cutter may include a snap spring that is attached to the disk spring and which provides an additional acceleration of the inner sleeve. The springs return the inner sleeve back to the original position when the control valve is switched to reduce the pressure of the drive chamber.

DETAILED DESCRIPTION OF THE INVENTION

The present invention is a guillotine surgical cutter. The cutter includes an inner sleeve that moves within the inner channel of an outer sleeve. The distal end of the outer sleeve may have a plurality of outer ports. The inner sleeve may also have an inner channel and one or more openings that are in fluid communication with the outer ports of the outer sleeve. The multiple openings increase the area of the cutting surface so that the cutter can cut more tissue per stroke. Additionally, the cutter can be operated so that the inner sleeve never completely blocks the outer ports so that there is not an instantaneous change in pressure during the cutting action of the device.

The inner sleeve can be connected to a diaphragm and a disk spring. The diaphragm is located adjacent to a drive chamber that is coupled to a source of pressurized air by a control valve. Actuation of the valve pressurizes the drive chamber and moves the inner sleeve relative to the outer sleeve. The cutter may include a snap spring that is attached to the disk spring and which provides an additional acceleration of the inner sleeve and an increase in the speed of the cutter. The springs return the inner sleeve back to the original position when the control valve is switched to reduce the pressure of the drive chamber. The cutter may have an additional valve that is coupled to a vacuum system which evacuates the drive chamber to further increase the speed of the cutter.

Figure 2:
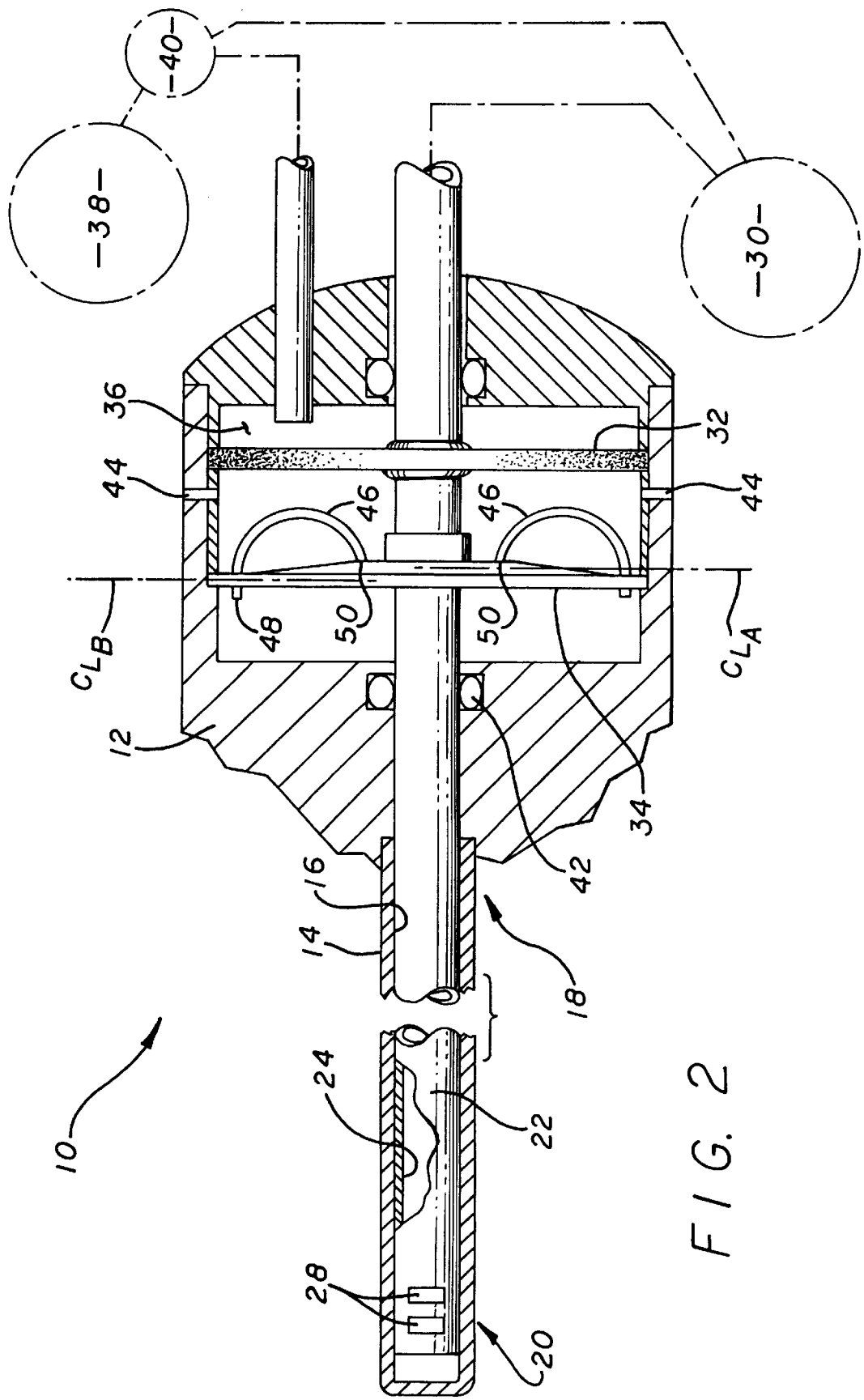
FIG. 2 is a cross-sectional view of a guillotine cutter of the present invention.

Referring to the drawings more particularly by reference numbers, FIG. 2 shows a surgical cutter 10 of the present invention. The cutter 10 includes a handpiece 12 that is held by an end user such as a surgeon. Attached to the handpiece 12 is an outer sleeve 14. The outer sleeve 14 has an inner channel 16 that extends from a proximal end 18 to a distal end 20 of the sleeve 14. Extending through the inner channel 16 is an inner sleeve 22. The inner sleeve 22 also has an inner channel 24.

Figure 1:
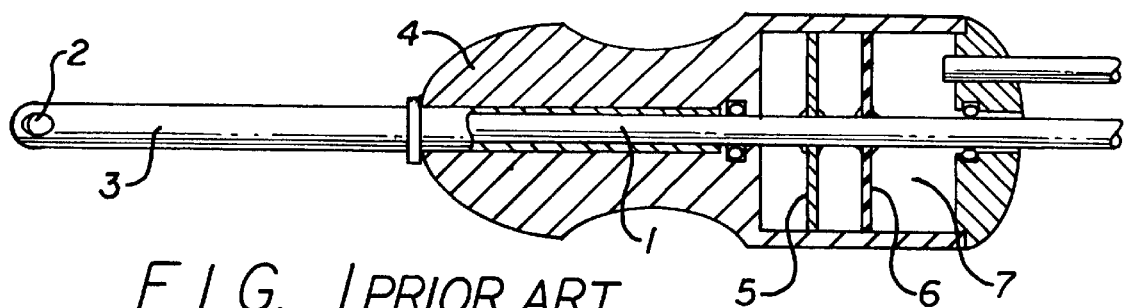
FIG. 1 is a cross-sectional view of a guillotine cutter of the prior art.
Figure 3:
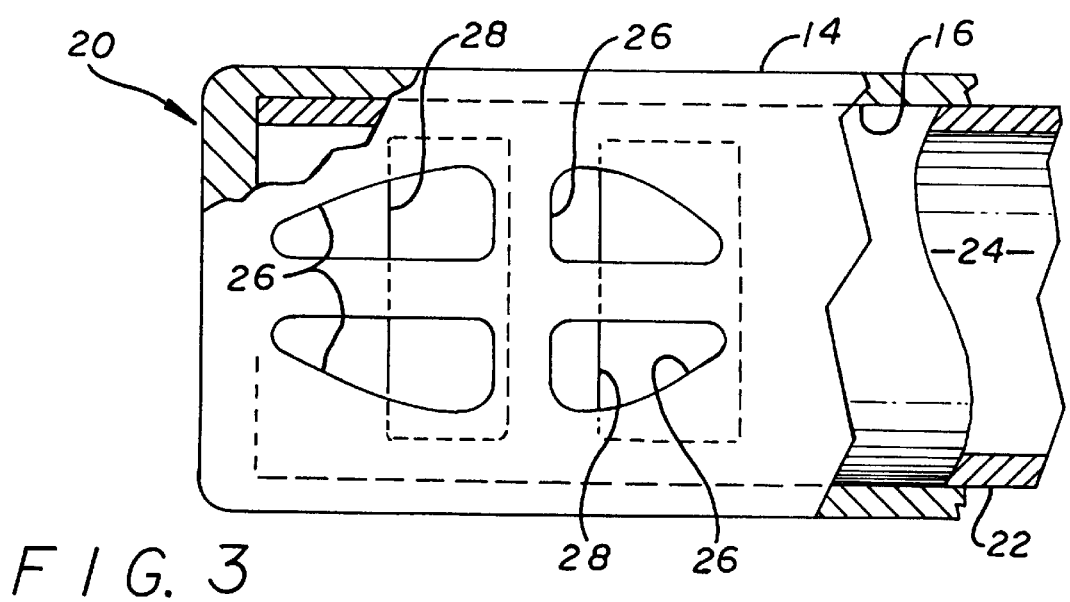
FIG. 3 is an enlarged view of a tip of the guillotine cutter.

As shown in FIG. 3, the distal end 20 of the outer sleeve 14 may have a plurality of outer ports 26. The inner sleeve 22 may also have a plurality of openings 28. Each opening 28 may be associated with a pair of outer ports 26. The inner sleeve 22 moves within the inner channel 16 of the outer sleeve 14. In one embodiment, the outer sleeve 14 has four outer ports 26 which create eight cutting surfaces, four cutting surfaces for each pass of the inner sleeve 22.

There is a negative pressure within the inner channel 24 of the inner sleeve 22 so that tissue is pulled into the ports 26 and then severed in reaction to relative movement between the inner 22 and outer 14 sleeves. The dual openings 28 and multiple ports 26 allow the inner sleeve 22 to cut when moving from the proximal to distal positions, and then out again when moving from the distal to the proximal positions. The cutter of the present invention can thus cut eight cuts per full cycle. In one embodiment, the outer ports 26 are always in fluid communication with the inner channel 24 of the inner sleeve 22 so that tissue can always be pulled into the ports 26. Additionally, the continuous fluid communication prevents instantaneous changes in pressure at the surgical site.

The outer ports 26 may have a triangular shape which creates force concentrator in the corners of the ports 26. Concentrating the cutting forces increases the efficiency of the cutter and minimizes tearing of the tissue. The rectangular openings 28 of the inner sleeve 22 also create a sharp cutting edge adjacent to the outer ports 26. Although a triangular shape is shown and described, it is to be understood that other shapes may be used in the present invention. For example, each port 26 may be shaped as a segment of a circle.

Referring to FIG. 2, the inner channel 24 of the inner sleeve 22 is coupled to a source of vacuum pressure 30 which aspirates tissue and other matter pulled through the outer ports 26. The inner sleeve 22 is also connected to a diaphragm 32 and a disk spring 34. The outer edge of the disk spring 34 is also attached to the handpiece 12. The diaphragm 30 is located adjacent to a drive chamber 36. The drive chamber 36 is relatively small to minimize the fluidic capacitance of the chamber 36. Minimizing the fluidic capacitance allows the chamber 36 to be quickly pressurized and depressurized to increase the speed of the cutter 10.

The drive chamber 36 is coupled to a source of pressurized air 38 by a control valve 40. The control valve 40 may be a three-way valve which couples the drive chamber 36 to either the pressurized air source 38 or the vacuum source 30. Coupling the drive chamber 36 to the vacuum source 30 will decrease the time required to evacuate the drive chamber 34 and increase the speed of the cutter 10. Alternatively, the control valve 40 may couple the drive chamber 36 to the pressurized air source 38 and the ambient. The handpiece 12 may contain O-rings 42 to seal the inner sleeve 22. The handpiece 12 may also have vent ports 44 to prevent a build up of pressure within the handpiece that would impede the movement of the diaphragm 32.

Figure 4:
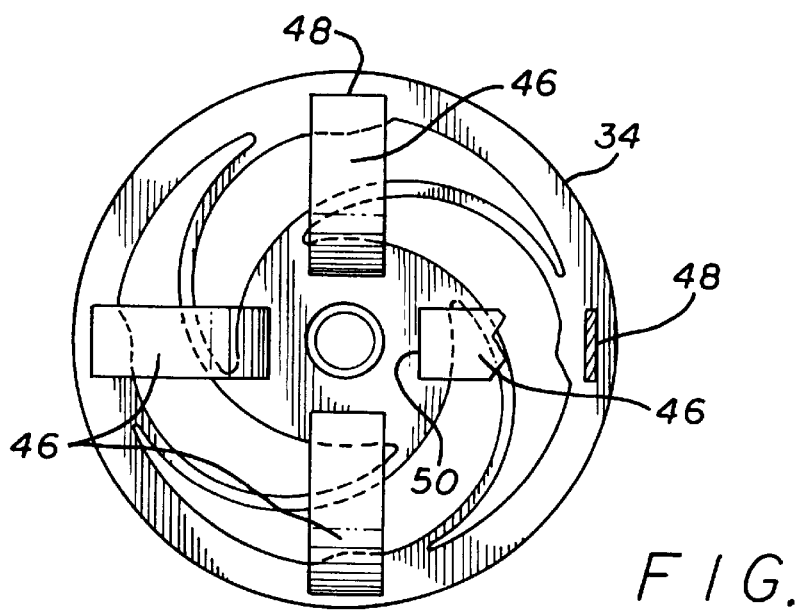
FIG. 4 is a top view of a return spring of the guillotine cutter.

The cutter 10 may have a plurality of snap rings 46 that are attached to the disk spring 34. The snap rings 46 may be C-shaped and have a first end 48 attached to an outer diameter of the disk spring 34 and a second end 50 attached to an inner diameter of the disk spring 34. As shown in FIG. 4, there may be four snap springs 46 equally spaced about the disk spring 34.

Referring to FIG. 2, the inner diameter of the disk spring 34 is preferably offset from the outer diameter of the disk spring 34. When the inner sleeve 22 moves toward the distal end of the outer sleeve 26 the centerline $C_{LA}$ of the inner disk diameter moves past the centerline $C_{LB}$ of the outer disk diameter at which point the snap springs 46 provide an over-center action which increases the acceleration of the inner sleeve 22 and the speed of the cutter 10.

In operation, the control valve 40 is actuated to pressurize the drive chamber 36 and expand the diaphragm 30. Expansion of the diaphragm 30 moves the inner sleeve 22 which cuts tissue pulled into the outer ports 26. The valve 40 is then switched to evacuate the drive chamber 36, wherein the disk 34 and snap 46 springs return the inner sleeve 22 to the original position where the process can be repeated.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A surgical cutter, comprising:

a handpiece;

an outer sleeve that is attached to said handpiece and which has an inner channel that extends from a proximal end to a distal end of said outer sleeve, said distal end of said outer sleeve having an outer port;

an inner sleeve that is located within said inner channel of said outer sleeve;

a disk spring that is attached to said inner sleeve and said handpiece;

a snap ring that is attached to said disk spring; and, a driver that moves said inner sleeve within said inner channel of said outer sleeve.

2. The surgical cutter as recited in claim 1, wherein said snap ring has a first end attached to an outer diameter of said disk spring and a second end attached to an inner diameter of said disk spring.

3. The surgical cutter as recited in claim 2, wherein said inner diameter is offset from said outer diameter of said disk spring.

4. The surgical cutter as recited in claim 1, wherein said driver includes a source of pressurized fluid that is in fluid communication with a membrane that is attached to said inner sleeve, and a control valve that controls the pressurized fluid.

5. The surgical cutter as recited in claim 1, wherein said inner sleeve has a pair of openings in fluid communication with an inner channel of said inner sleeve.

6. The surgical cutter as recited in claim 5, wherein each opening of said inner sleeve is coupled to a pair of outer ports of said outer sleeve.

* * * * *